(12) United States Patent
Feng et al.

(10) Patent No.: US 12,410,131 B2
(45) Date of Patent: Sep. 9, 2025

(54) METHOD FOR PREPARATION OF TRANS-N-BENZYLOXYCARBONYL-(3-HYDROXY-2-PIPERIDINYL)-2-PROPANONE AS INTERMEDIATE OF HALOFUGINONE

(71) Applicant: CHENGDA PHARMACEUTICALS CO., LTD., Jiaxing (CN)

(72) Inventors: Yu Feng, Jiaxing (CN); Hong Xu, Jiaxing (CN); Jiaxuan Wu, Jiaxing (CN); Danhui Song, Jiaxing (CN); Weihui Zhong, Jiaxing (CN); Fei Ling, Jiaxing (CN); Chao Xu, Jiaxing (CN)

(73) Assignee: CHENGDA PHARMACEUTICALS CO., LTD., Jiaxing (CN)

( * ) Notice: Subject to any disclaimer, the term of this patent is extended or adjusted under 35 U.S.C. 154(b) by 496 days.

(21) Appl. No.: 18/065,636

(22) Filed: Dec. 14, 2022

(65) Prior Publication Data

US 2023/0192614 A1 Jun. 22, 2023

Related U.S. Application Data

(63) Continuation of application No. PCT/CN2022/086077, filed on Apr. 11, 2022.

(30) Foreign Application Priority Data

Oct. 21, 2021 (CN) .......................... 202111228375.X

(51) Int. Cl.
*C07D 211/42* (2006.01)
*C07D 211/02* (2006.01)

(52) U.S. Cl.
CPC .......... *C07D 211/42* (2013.01); *C07D 211/02* (2013.01); *C07B 2200/07* (2013.01)

(58) Field of Classification Search
CPC .. C07D 211/42; C07D 211/02; C07B 2200/07
See application file for complete search history.

(56) References Cited

U.S. PATENT DOCUMENTS

2022/0371995 A1* 11/2022 Jin .......................... C07C 69/76

FOREIGN PATENT DOCUMENTS

| CN | 103467449 A | 12/2013 |
| CN | 110452158 A | 11/2019 |
| CN | 113999164 A | 2/2022 |

OTHER PUBLICATIONS

International Search Report issued in corresponding International application No. PCT/CN2022/086077, mailed Jun. 21, 2022.
Written Opinion of the International Searching Authority for No. PCT/CN2022/086077.

* cited by examiner

*Primary Examiner* — Timothy R Rozof

(57) ABSTRACT

The present disclosure relates to the field of drug synthesis, and discloses a method for the preparation of trans-N-benzyloxycarbonyl-(3-hydroxy-2-piperidinyl)-2-propanone as an intermediate of halofuginone. In the preparation method according to the present disclosure, for the first time, trans-N-benzyloxycarbonyl-(3-hydroxy-2-piperidinyl)-2-propanone as shown in Formula I is obtained from amino-substituted pentanal and a thiazolyl sulfoxide compound as raw materials by Mislow-Evans rearrangement reaction and subsequent Lewis acid catalysis. The method for the preparation of trans-N-benzyloxycarbonyl-(3-hydroxy-2-piperidinyl)-2-propanone as an intermediate of halofuginone according to the present disclosure has high yields and stable qualities, provides a new reference route for the synthesis of trans-N-benzyloxycarbonyl-(3-hydroxy-2-piperidinyl)-2-propanone, avoids the reduction of pyridine, and overcomes the disadvantage of requiring the use of an expensive metal catalyst Rh/Al2O3.

10 Claims, No Drawings

METHOD FOR PREPARATION OF TRANS-N-BENZYLOXYCARBONYL-(3-HYDROXY-2-PIPERIDINYL)-2-PROPANONE AS INTERMEDIATE OF HALOFUGINONE

TECHNICAL FIELD

The present disclosure relates to the field of drug synthesis, and in particular to a method for the preparation of trans-N-benzyloxycarbonyl-(3-hydroxy-2-piperidinyl)-2-propanone as an intermediate of halofuginone.

BACKGROUND

Halofuginone, also known as tempostatin, is mainly found in the vegetation such as Dichroa febrifuga Lour. and *Hydrangea chinensis* Maxim. Clinical study results show that it has high antimalarial activity and is currently mainly used for the prevention and treatment of coccidiosis and cryptosporidiosis, and has become the drug of choice for the treatment of avian coccidiosis due to its advantages such as low residue, good insecticidal effect and strong resistance. The structure is shown as follows.

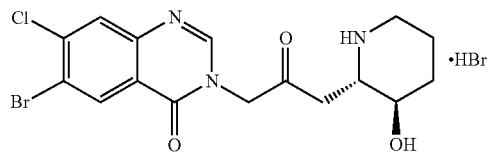 [SMILES: O=C(C[C@@H]1NCCC[C@H]1O)Cn1cnc2cc(Cl)c(Br)cc2c1=O ; Br]

Halofuginone

Through extensive literature study, it is found that the total synthesis about halofuginone requires completing the construction of the quinazoline fragment and the piperidine ring, and then ligating the two parts to synthesize halofuginone.

Among the numerous synthetic routes, the route for 7-bromo-6-chloro-4(3H)-quinazolinone by Baker's group is the earliest and most classical synthetic route, and also the one that has achieved industrial production. In terms of this route, the starting materials and the reagents required for the reaction are relatively inexpensive, the operation for each step is relatively common, and the reaction route is relatively mature. The reaction synthetic route is shown in Route I.

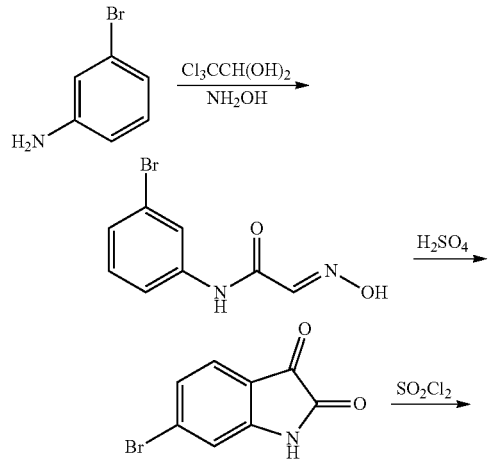

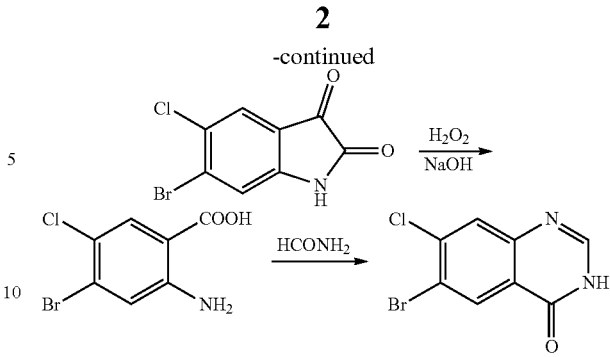

Route I

The piperidine ring fragment is the focus of this study. Trans-N-benzyloxycarbonyl-(3-hydroxy-2-piperidinyl)-2-propanone is an important intermediate of halofuginone, and the structure is shown in Formula I.

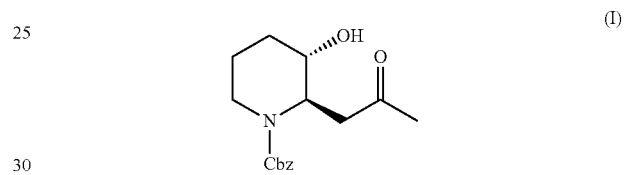

Among the known synthetic routes, the synthesis of intermediate 1, in which the hydroxyl group was methylated, was first reported by the Baker's study group in the United States, which acted as a complement to intermediate I. This compound was also used as an important intermediate in the synthesis of halofuginone for the synthesis of halofuginone. The synthetic route is shown in Route II.

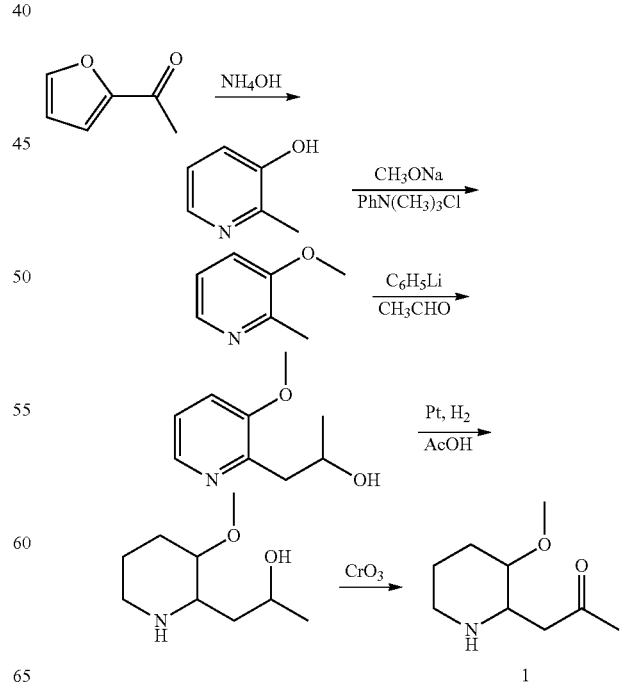

Route II

The synthesis of intermediate 1 was improved by Donald et al. on the basis of Baker et al, which is disclosed in J Org Chem, 1973, 38(10): 1933-1937. The synthetic route is shown in Route III:

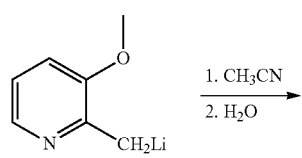

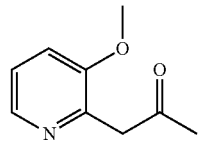

Route III

Later, the synthesis of intermediate 1 was improved by Shen Changmao et al. in China on the basis of Baker et al. The synthetic route is shown in Route IV:

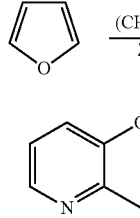

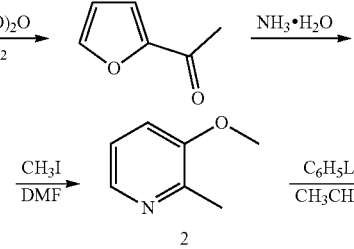

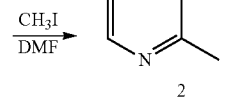

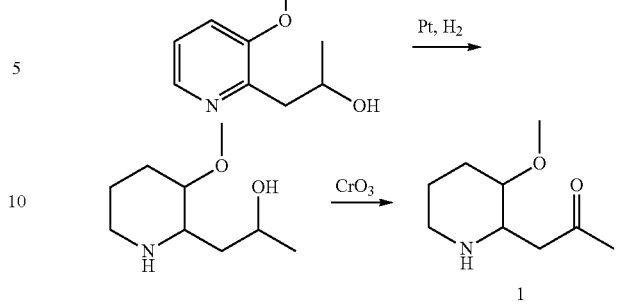

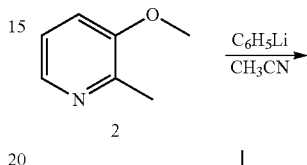

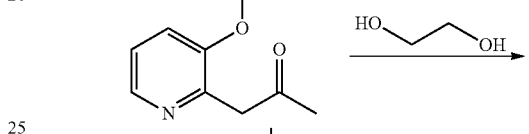

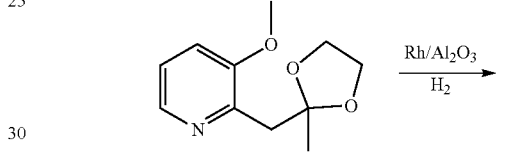

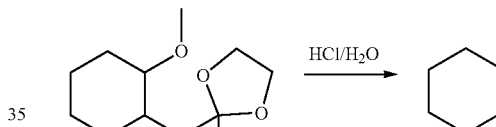

Route IV

In 1996, a total synthesis route was reported by the Burgess's group. The synthetic route is shown in Route V.

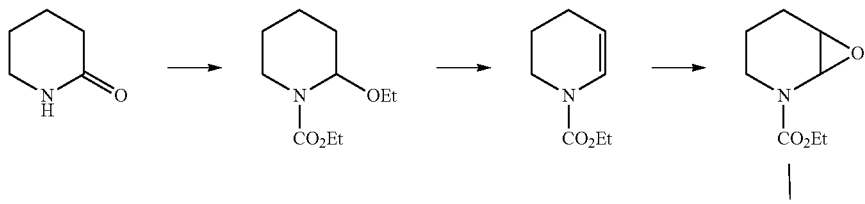

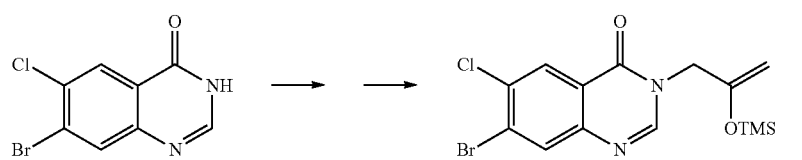

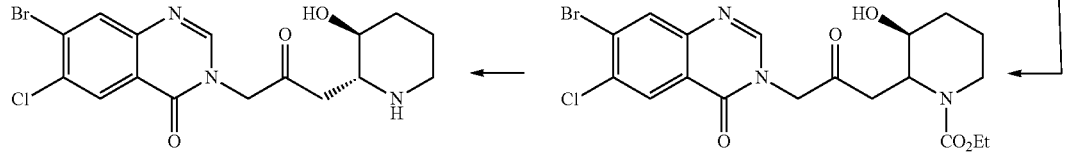

Route V

In 2001, a seven-step synthesis of a piperidine ring fragment derivative for halofuginone ligation reaction from 3-hydroxypyridine as a raw material was reported by Takeuchi et al. The synthetic route is shown in Route VI.

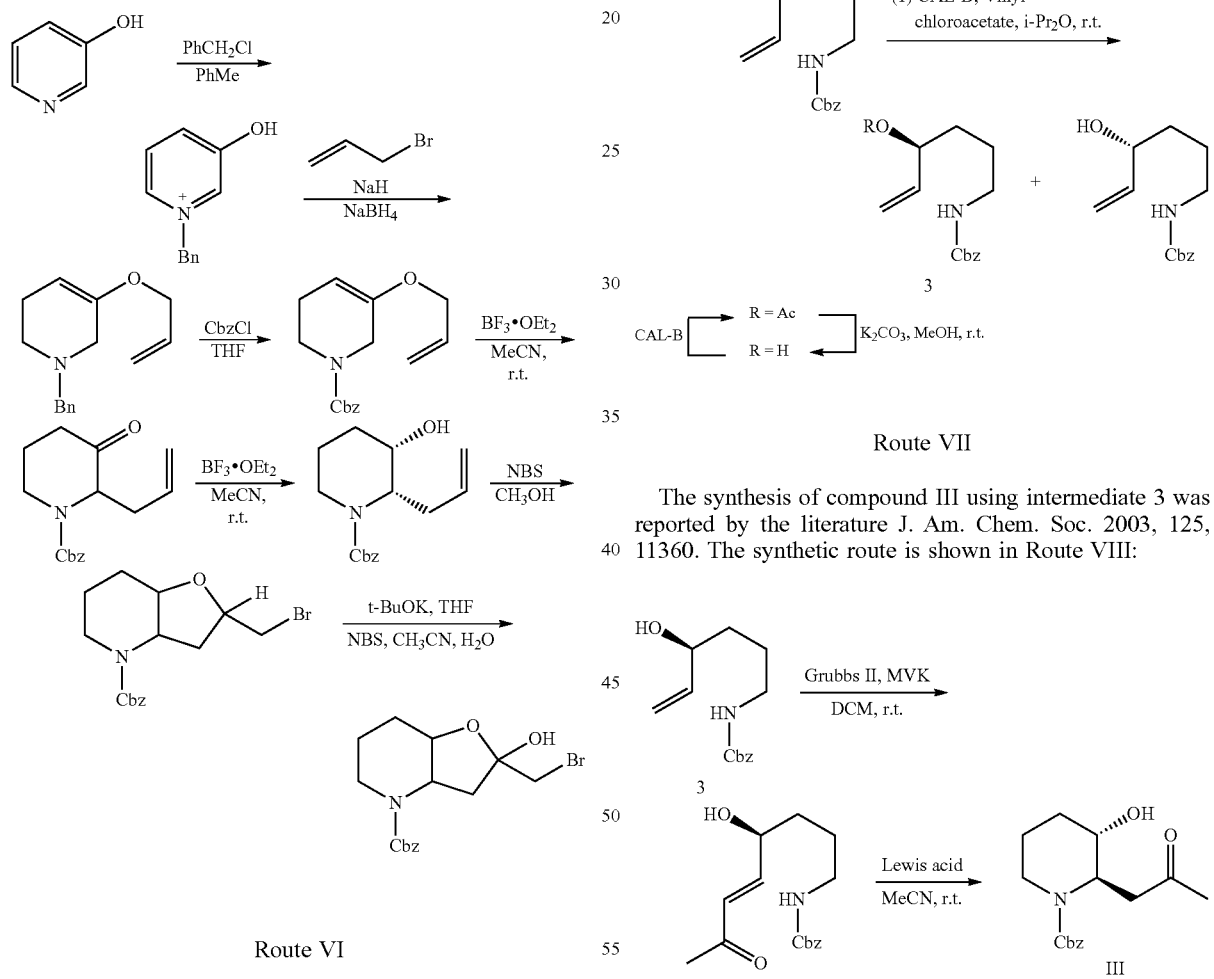

Route VI

Also, the synthesis of Intermediate 3 was reported in the literature Chem. Lett. 1987, 16, 2091. The synthetic route is shown in Route VII:

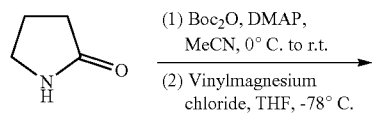

Route VII

The synthesis of compound III using intermediate 3 was reported by the literature J. Am. Chem. Soc. 2003, 125, 11360. The synthetic route is shown in Route VIII:

Route VIII

After analyzing the above synthetic routes, it is found that the key lies in the synthesis of the piperidine ring, and the reported routes have the following deficiencies:

Although Route II is a classical route, it has a low overall yield and mainly serves as a guide for subsequent studies.

In Route III, lithium reagents are inevitably used as deprotonation reagents, which results in high reaction costs and labor protection intensity. In addition, the route relates to the use of an Rh/Al$_2$O$_3$ catalyst, and the price of this catalyst remains high for a long time, which results in high production costs. Also, the method is prone to reduce carbonyl groups and has a poor selectivity, in which intermediate 1 exists in both cis and trans configurations, and the yield of trans is not high.

In Route IV, intermediate 1 is synthesized from furan as a raw material, but highly toxic methylation reagents are used. In addition, in order to improve the selectivity of reduction, two options are provided for the treatment of intermediate 2: one option comprising firstly reducing the intermediate to an alcohol and then oxidizing the alcohol to a ketone using Jones reagent, which brings the problem of a long route and the introduction of toxic metal chromium ions; and the other comprises firstly protecting the ketone as an acetal, then reducing and finally deprotecting, which brings the problem of a long route and a complex workup. In addition, the lithium reagents with a high labor protection intensity and a complex workup as well as an expensive Rh/Al$_2$O$_3$ catalyst are used for both options.

In Route V invented by the authors, a racemic compound of halofuginone is obtained by firstly preparing a silyl enol ether structure containing side chains with a quinazolinone, modifying the piperidine ring as an epoxy structure, and then carrying out a selective addition under Lewis acid conditions at the position with many substituents to complete a fragment ligation. Although the synthetic route has only seven steps, it has the problems such as a total yield of only 0.5%, high risk factor brought by using NaH, and harsh total reaction conditions.

Route VI has the hidden danger of violent exothermic reaction with the use of methanol. A large amount of CbzCl is used, the workup is troublesome and many isomers will be produced.

In route VII, intermediate 3 is prepared through Boc protection, Grignard reaction, Luche reduction, deprotection, Cbz protection and configuration transformation. This route has the problems such as difficult tri-wastes treatment brought by magnesium salt of Grignard reagent, long route and low proportion of trans-configuration.

In route VIII, compound III, which is the focus of our study, is synthesized with intermediate 3. However, this route is costly since Grubbs reagent is expensive and intermediate 3 has few sources and is expensive.

In view of the above, a synthetic method with a high yield, a stable quality and a low cost is urgently needed.

SUMMARY

The technical problem to be solved by the present disclosure is:

A method for the preparation of trans-N-benzyloxycarbonyl-(3-hydroxy-2-piperidinyl)-2-propanone is provided. According to the present disclosure, for the first time, compound II is generated from thiazolyl sulfoxide compound III and amino-substituted pentanal IV as raw materials through Sulfinyl-Knoevenagel condensation and Mislow-Evans rearrangement; and trans-compound I is generated by cyclizing compound II under the induction of Lewis acid. This route is less costly due to the avoidance of an expensive Rh/Al2O3 catalyst, has convenient workups due to the avoidance of hazardous lithium reagents, and has mild conditions.

The purpose according to the present disclosure is to solve the above problems in the prior art and to provide a method for the preparation of trans-N-benzyloxycarbonyl-(3-hydroxy-2-piperidinyl)-2-propanone as an intermediate of halofuginone.

To achieve the above purpose, the following technical solution is used in the present disclosure:

A method for the preparation of trans-N-benzyloxycarbonyl-(3-hydroxy-2-piperidinyl)-2-propanone as an intermediate of halofuginone with the following synthetic route:

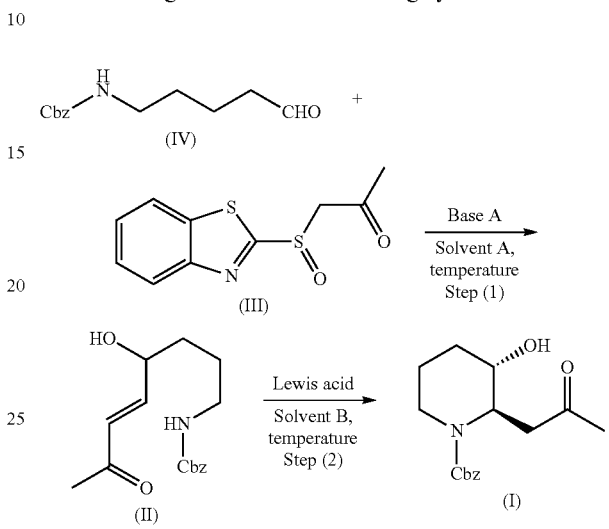

The synthesis method comprises the following steps:

(1) subjecting amino-substituted pentanal as shown in Formula IV with a thiazolyl sulfoxide compound as shown in Formula III in the presence of a base to Sulfinyl-Knoevenagel and Mislow-Evans rearrangement reaction to obtain α,β-unsaturated ketone as shown in Formula II;

(2) obtaining trans-N-benzyloxycarbonyl-(3-hydroxy-2-piperidinyl)-2-propanone as shown in Formula I under the catalysis of Lewis acid with the following synthetic route:

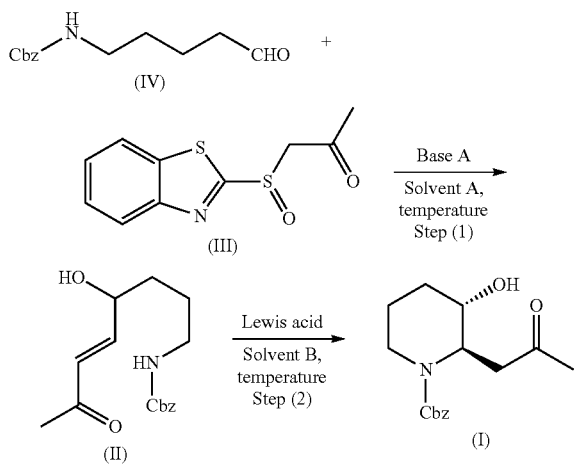

As a further improvement of this solution, the synthetic route of the thiazolyl sulfoxide compound as shown in Formula III is as follows:

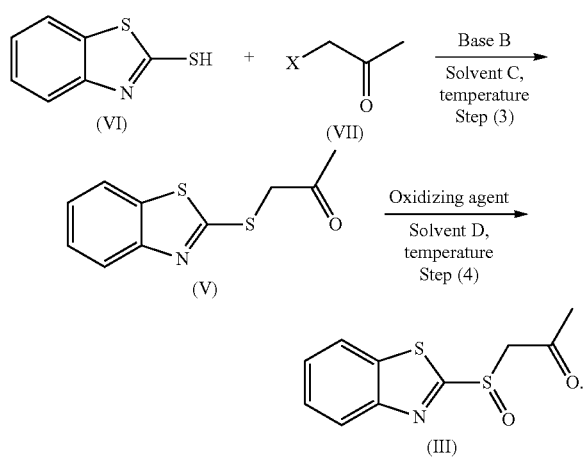

The synthesis method comprises the following steps:
(1) subjecting a thiazolyl thiol as shown in Formula VI with α-haloacetone as shown in Formula VII to a substitution reaction to obtain thiazolyl thioether as shown in Formula V;
(2) oxidizing the thiazolyl thioether with an oxidizing agent to obtain the thiazolyl sulfoxide compound as shown in Formula III.

As a further improvement of this solution, the synthetic route of the amino-substituted pentanal as shown in Formula IV is as follows:

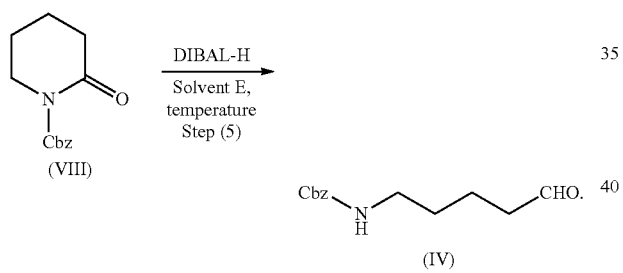

The synthesis method comprises: reducing the piperidone as shown in Formula VIII with DIBAL-H to obtain the amino-substituted pentanal as shown in Formula IV.

As a further improvement of this solution, in step (1), the organic solvent A is any one or more of dichloromethane, ethanol, isopropanol, acetonitrile, trimethyl phosphite, tetrahydrofuran, N,N-dimethylacetamide, N,N-dimethylformamide or ethyl acetate, and the amount of organic solvent A by mass is 3 to 30 times that of compound VI.

As a further improvement of this solution,
in step (1), the base A as a base is selected from organic bases or inorganic bases, and the organic base is selected from any one of sodium hydride, sodium methoxide, pyridine, piperidine, potassium tert-butoxide, sodium tert-butoxide, butyllithium, 4-dimethylaminopyridine, N,N-diisopropylethylamine or triethylamine; and the inorganic base is selected from any one of sodium hydroxide, potassium hydroxide, potassium carbonate, potassium phosphate or sodium carbonate; and
in step (1), the molar ratio of compound VI, compound VII and base A is 1:(1.0-3.0):(1.0-3.0).

As a further improvement of this solution, in step (2), the organic solvent B is any one of dichloromethane, ethanol, isopropanol, acetonitrile, trimethyl phosphite, tetrahydrofuran, N,N-dimethylacetamide, N,N-dimethylformamide or ethyl acetate, and the amount of organic solvent B by mass is 2 to 30 times that of compound II; and in step (2), the reaction is carried out at a suitable temperature for a suitable time;
in step (2), the Lewis acid is any one of aluminum trichloride, boron trifluoride diethyl etherate, iron trichloride, and zinc chloride; and
in step (2), the molar ratio of compound II and Lewis acid is 1:(0.05-0.10).

As a further improvement of this solution, in step (3), the organic solvent C is any one of dichloromethane, ethanol, isopropanol, acetonitrile, tetrahydrofuran, N,N-dimethylacetamide, N,N-dimethylformamide or ethyl acetate, and the amount of organic solvent C by mass is 5 to 50 times that of compound VI;
in step (3), the base B is selected from organic bases or inorganic bases, and the organic base is selected from any one of sodium hydride, sodium methoxide, potassium tert-butoxide, sodium tert-butoxide, butyllithium, 4-dimethylaminopyridine, N,N-diisopropylethylamine or triethylamine; the inorganic base is selected from any one of sodium hydroxide, potassium hydroxide, potassium carbonate, potassium phosphate or sodium carbonate; and X represents any one of chlorine, bromine, and iodine; and in step (3), the molar ratio of compound VI, haloacetone and base is 1:(1.0-2.0):(1.0-2.0).

As a further improvement of this solution, in step (4), the organic solvent D is one of dichloromethane, ethanol, isopropanol, acetic acid, acetonitrile, tetrahydrofuran, N,N-dimethylacetamide, N,N-dimethylformamide or ethyl acetate, and the amount of organic solvent D by mass is 3 to 50 times that of compound V;
in step (4), the oxidizing agent is any one of hydrogen peroxide, m-chloroperoxybenzoic acid, and peroxyacetic acid; and
in step (4), the molar ratio of compound V and oxidizing agent is 1:(0.80-3.0).

As a further improvement of this solution, in step (5), the organic solvent E is the organic solvent B, which is any one of dichloromethane, 1,2-dichloroethane, ethanol, isopropanol, trifluoroethanol, acetonitrile, tetrahydrofuran or ethyl acetate, and the amount of organic solvent B by mass is 3 to 50 times that of compound VIII.

As a further improvement of this solution, in step (5), the reducing agent is diisopropylaluminium hydride, and the molar ratio of compound VIII and reducing agent is 1:(1.0-4.0).

Compared with the prior art, the present disclosure has the following beneficial effects:
a) for the first time, trans-N-benzyloxycarbonyl-(3-hydroxy-2-piperidinyl)-2-propanone as shown in Formula I is obtained from amino-substituted pentanal and a thiazolyl sulfoxide compound as raw materials by Mislow-Evans rearrangement reaction and subsequent Lewis acid catalysis, and this route has high yields and stable qualities, and provides a new reference route for the synthesis of trans-N-benzyloxycarbonyl-(3-hydroxy-2-piperidinyl)-2-propanone;
b) the use of an expensive metal catalyst Rh/Al2O3 is avoided; and c) the use of hazardous lithium reagents is avoided and labor protection intensity is reduced, which have some guidance for industrialization.

DETAILED DESCRIPTION

In order to make the purposes, technical solutions and advantages according to the present disclosure clearer, the present disclosure is further described with the following examples:

Example 1

Preparation of Compound IV

Compound VIII: DIBAL-H:tetrahydrofuran=1:1.2:56.3.

(1) In a 20 mL three-necked flask, compound VIII (300 mg, 1.3 mmol) was dissolved in dry tetrahydrofuran (6 mL), the temperature was controlled at −78° C., and DIBAL-H (1 M, 1.54 mL, 1.54 mmol) was slowly added dropwise. The reaction was incubated for 1 h, and the reaction was monitored by TLC until completed. Saturated ammonium chloride solution (10 g) was added and stirred well to form a white solid layer. The white solid layer was diluted by adding ethyl acetate and filtered with diatomaceous earth, and the filtrate was extracted and partitioned with ethyl acetate. The organic phase was dried over anhydrous sodium sulfate, dried via rotary evaporation, and directly used in the next reaction step.

Preparation of Intermediate V

Compound VI: bromoacetone:potassium carbonate:N,N-dimethylformamide=1:1.2:1.2:23.0.

(2) In a 2 L three-necked flask, compound VI (13.9 g, 0.08 mol) and potassium carbonate (13.8 g, 0.1 mol) were added to N,N-dimethylformamide (65 mL), and stirred well at a room temperature of 30° C. A solution of bromoacetone (13.9 g, 0.1 mol) in N,N-dimethylformamide (85 mL) was added slowly under the protection of nitrogen and the reaction was vigorously exothermic. The reaction was stirred for 1 h. The reaction system changed from yellow to brown, and the reaction was monitored by TLC until completed. The reaction was washed by adding 2×250 mL of water and extracted with 150 mL of ethyl acetate. The organic phase was concentrated under reduced pressure to obtain a brown crude product, which was purified by column chromatography to obtain 13.4 g of compound V in 78% yield and 96% purity by HPLC.

Graphical characterization of compound V:
$^1$H NMR (600 MHz, CDCl$_3$): δ 7.86 (d, J=8.4 Hz, 1H), 7.77 (d, J=8.4 Hz, 1H), 7.74 (t, J=7.8 Hz, 1H), 7.32 (t, J=7.8 Hz, 1H), 4.26 (s, 2H), 2.42 (s, 3H); $^{13}$C NMR (150 MHz, CDCl$_3$): δ 201.8, 165.0, 152.8, 135.5, 126.1, 124.5, 121.5, 121.1, 43.1, 28.9; MS (ESI) m/z calcd for C$_{10}$H$_9$NOS$_2$ [M+H]$^+$ 224.0, found 224.0.

Preparation of Intermediate III

Compound V: m-chloroperoxybenzoic acid:dichloromethane=1:0.95:122.0.

(3) In a 20 mL three-neck flask, compound V (330 mg, 1.48 mmol) was dissolved in dichloromethane (15 g), the temperature was controlled at −10-0° C., and m-chloroperoxybenzoic acid (284 mg, 1.40 mmol) was added in three batches at half-hour intervals. The reaction was completed after incubating for 1 h. The reaction was quenched by adding saturated sodium thiosulfate solution (20 mL). The aqueous phase and organic phase were separated. The aqueous phase was extracted with dichloromethane (15 mL), and the organic phases were combined. The organic phase was washed twice with saturated sodium bicarbonate solution (10 mL, 15 mL), then washed with saturated sodium chloride solution (10 mL), and dried via rotary evaporation to obtain 450 mg of crude product, which was separated by column chromatography to obtain 282.9 mg of product as a white solid in 80.2% yield.

Graphical Characterization of Compound III:
$^1$H NMR (400 MHz, CDCl$_3$): δ 7.26-8.09 (m, 4H), 4.36 (d, J=14.8 Hz, 1H), 4.22 (d, J=14.8 Hz, 1H), 2.37 (s, 3H); $^{13}$C NMR (100 MHz, CDCl$_3$): δ 198.3, 175.9, 153.7, 136.2, 127.2, 126.5, 124.1, 122.4, 67.7, 31.8; MS (ESI) m/z calcd for C$_{10}$H$_9$NO$_2$S$_2$[M+H]$^+$ 240.1, found 240.1.

Preparation of Intermediate II

Compound III: compound IV: piperidine:trimethyl phosphite:acetonitrile=1:1.5:1.0:1.0:95.0.

(4) In a 20 mL three-necked flask, compound III (119 mg, 0.5 mmol) was dissolved in acetonitrile (5 mL) and compound IV (176 mg, 0.75 mmol), piperidine (85 mg, 1.0 mmol) and trimethyl phosphite (62 mg, 0.5 mmol) were added at 25° C. The reaction was completed after reacting at 25° C. for 5 h. The reaction was quenched by adding saturated ammonium chloride solution (5 mL). Ethyl acetate was added for extraction (3×5 mL), and the aqueous phase and the organic phase were separated. The organic phase was dried over anhydrous magnesium sulfate, and dried via rotary evaporation to obtain 138 mg of crude product, which was separated by column chromatography to obtain 124.9 mg of product as a light brown oil in 85.2% yield.

Graphical Characterization of Compound II:
$^1$H NMR (400 MHz, CDCl$_3$): δ 7.29-7.41 (m, 5H), 6.73 (m, 1H), 6.26 (d, J=16.0 Hz, 1H), 5.11 (s, 2H), 4.91 (br. s, 1H), 4.13-4.41 (m, 1H), 3.18-3.31 (m, 2H), 2.21-2.38 (m, 1H), 2.29 (s, 3H), 1.53-1.76 (m, 4H); $^{13}$C NMR (CDCl$_3$, 100 MHz): δ 198.1, 155.6, 149.4, 136.5, 129.3, 127.5, 127.2, 127.1, 71.8, 66.6, 40.8, 33.1, 27.4, 26.1.

Preparation of Intermediate I

Compound II: boron trifluoride diethyl etherate:acetonitrile=1:0.07:191.0.

(5) In a 2 L three-necked flask, compound II (145.5 mg, 0.5 mmol) was dissolved in acetonitrile (5 mL), a solution of boron trifluoride diethyl etherate (10 mg, 0.07 mmol) in acetonitrile (1 mL) was added dropwise at a room temperature of 30° C., and then stirred for 0.5 h. The reaction solution was added with dichloromethane (5 mL), quenched with saturated sodium bicarbonate (10 mL), and separated. The organic phase was washed with saturated brine (10 mL) and partitioned. The organic phase was dried over anhydrous sodium sulfate, filtered, and dried via rotary evaporation to obtain 130.9 mg of crude product, which was purified by column chromatography to obtain 101.9 mg of compound I as a bright yellow oil in 70% yield.

Graphical Characterization of Compound I:
$^1$H NMR (400 MHz, CDCl$_3$): δ 7.28-7.39 (m, 5H), 5.13 (s, 2H), 4.73 (br. t, 1H), 4.07 (br. d, 1H), 3.78-3.88 (m, 1H), 2.87 (br. t, 1H), 2.65 (d, J=7.0 Hz, 2H), 2.04-2.26 (m, 3H), 1.60-1.99 (m, 3H), 1.34-1.47 (m, 1H); $^{13}$C NMR (100 MHz, CDCl$_3$): δ 205.7, 156.0, 136.3, 128.2, 127.8, 127.6, 67.1, 67.0, 54.0, 43.5, 39.4, 30.0, 25.7, 18.7.

Example 2

Preparation of Compound IV

Compound VIII: DIBAL-H:tetrahydrofuran=1:1.2:56.3.

(1) In a 20 mL three-necked flask, compound VIII (310 mg, 1.3 mmol) was dissolved in dry tetrahydrofuran (6 mL), the temperature was controlled at −40° C., and DIBAL-H (1 M, 1.54 mL, 1.54 mmol) was slowly added dropwise. The reaction was incubated for 1.5 h, and the reaction was monitored by TLC until completed. Saturated ammonium chloride solution (10 g) was added and stirred well to form a white solid layer. The white solid layer was diluted by adding ethyl acetate and filtered with diatomaceous earth, and the filtrate was extracted and partitioned with ethyl acetate. The organic phase was dried over anhydrous sodium sulfate, dried via rotary evaporation, and directly used in the next reaction step.

Preparation of Intermediate V

Compound VI: bromoacetone:potassium carbonate:tetrahydrofuran=1:1.2:1.2:22.8.

(2) In a 2 L three-necked flask, compound VI (1.39 g, 8 mmol) and potassium carbonate (1.38 g, 10 mmol) were added to tetrahydrofuran (6.5 mL), and stirred well at a room temperature of 30° C. A solution of bromoacetone (1.39 g, 10 mmol) in tetrahydrofuran (8.5 mL) was added slowly under the protection of nitrogen and the reaction was vigorously exothermic. The reaction was stirred for 1 h. The reaction system changed from yellow to brown, and the reaction was monitored by TLC until completed. The solvent was removed by concentration under reduced pressure. The crude product was purified by column chromatography to obtain 0.95 g of compound V in 55.1% yield.

Preparation of Intermediate III

Compound V: m-chloroperoxybenzoic acid:1,2-dichloroethane=1:0.95:61.5.

(3) In a 20 mL three-neck flask, compound V (330 mg, 1.48 mmol) was dissolved in 1,2-dichloroethane (9 g), the temperature was controlled at −10-0° C., and m-chloroperoxybenzoic acid (284 mg, 1.40 mmol) was added in three batches at half-hour intervals. The reaction was completed after incubating for 1 h. The reaction was quenched by adding saturated sodium thiosulfate solution (20 mL). The organic solvent was removed via rotary evaporation, and EA was added for extraction (2×10 mL). The aqueous phase and organic phase were separated. The organic phase was washed twice with saturated sodium bicarbonate solution (10 mL, 15 mL), then washed with saturated sodium chloride solution (10 mL), and dried via rotary evaporation to obtain 410 mg of crude product, which was separated by column chromatography to obtain 252.2 mg of product as a white solid in 71.5% yield.

Preparation of Intermediate II

Compound III: compound IV: piperidine:toluene=1:1.5:2.0: 47.3.

(4) In a 20 mL three-necked flask, compound III (119 mg, 0.5 mmol) was dissolved in toluene (5 mL) and compound IV (176 mg, 0.75 mmol) and piperidine (85 mg, 1.0 mmol) were added at 25° C. The reaction was completed after reacting at 25° C. for 5 h. The reaction was quenched by adding saturated ammonium chloride solution (5 mL). Ethyl acetate was added for extraction (3×5 mL). The organic phases were combined, washed with saturated brine, dried over anhydrous magnesium sulfate, and dried via rotary evaporation. The residue was separated by column chromatography to obtain 108.6 mg of product as a colorless oil in 74.1% yield.

Preparation of Intermediate I

Compound II: boron trifluoride diethyl etherate:methanol=1: 0.07:296.4.

(5) In a 2 L three-necked flask, compound II (145.5 mg, 0.5 mmol) was dissolved in methanol (5 mL), a solution of boron trifluoride diethyl etherate (10 mg, 0.07 mmol) in methanol (1 mL) was added dropwise at a room temperature of 30° C., and then stirred for 0.5 h. The reaction was quenched with saturated sodium bicarbonate (10 mL), and the methanol solution was removed under reduced pressure. The reaction solution was added with dichloromethane (5 mL) and partitioned. The solution was washed with saturated brine (10 mL), and the organic phase was separated, dried over anhydrous sodium sulfate, filtered, and dried via rotary evaporation. The residue was purified by column chromatography to obtain 72.8 mg of compound I in 50% yield.

Example 3

Preparation of Compound IV

Compound VIII: DIBAL-H:tetrahydrofuran=1:1.2:56.3.

(1) In a 20 mL three-necked flask, compound VIII (310 mg, 1.3 mmol) was dissolved in dry tetrahydrofuran (6 mL), the temperature was controlled at −30° C., and DIBAL-H (1 M, 1.54 mL, 1.54 mmol) was slowly added dropwise. The reaction was incubated for 1.5 h, and the reaction was monitored by TLC until completed. Saturated ammonium chloride solution (10 g) was added and stirred well to form a white solid layer. The white solid layer was diluted by adding ethyl acetate and filtered with diatomaceous earth, and the filtrate was extracted and partitioned with ethyl acetate. The organic phase was dried over anhydrous sodium sulfate, dried via rotary evaporation, and directly used in the next reaction step.

Preparation of Intermediate V

Compound VI: bromoacetone:potassium tert-butoxide:N,N-dimethylformamide=1:1.2:1.2:25.0.

(2) In a 2 L three-necked flask, compound VI (1.39 g, 8 mmol) and potassium tert-butoxide (1.12 g, 10 mmol) were added to N,N-dimethylformamide (6.5 mL), and stirred well at a room temperature of 30° C. A solution of bromoacetone (1.39 g, 10 mmol) in N,N-dimethylformamide (8.5 mL) was added slowly under the protection of nitrogen and the reaction was vigorously exothermic. The reaction was stirred for 1 h. The reaction system changed from yellow to brown, and the reaction was monitored by TLC until completed. The solvent was removed by concentration under reduced pressure. The crude product was purified by column chromatography to obtain 1.12 g of compound V in 65.4% yield.

Preparation of Intermediate III

Compound V: hydrogen peroxide solution:dichloromethane=1:1:61.5.

(3) In a 20 mL three-neck flask, compound V (330 mg, 1.48 mmol) was dissolved in dichloromethane (15 g), the temperature was controlled at −10-0° C., and 30% hydrogen peroxide solution (1.48 mmol) was slowly added dropwise. The reaction was completed after incubating for 1 h. The reaction was quenched by adding saturated sodium thiosulfate solution (20 mL). The organic solvent was removed via rotary evaporation, and EA was added for extraction (2×10 mL). The aqueous phase and organic phase were separated. The organic phase was washed twice with saturated sodium bicarbonate solution (10 mL, 15 mL), then washed with saturated sodium chloride solution (10 mL), and dried via rotary evaporation. The residue was separated by column chromatography to obtain 126.6 mg of product as a white solid in 35.9% yield.

Preparation of Intermediate II

Compound III: compound IV: 2-methylaminopyridine:trimethyl phosphite:acetonitrile=1:1.5:2.0:1.0:95.0.

(4) In a 20 mL three-necked flask, compound III (119 mg, 0.5 mmol) was dissolved in acetonitrile (5 mL) and compound IV (176 mg, 0.75 mmol), 2-methylaminopyridine (122 mg, 1.0 mmol) and trimethyl phosphite (62 mg, 0.5 mmol) were added at 25° C. The reaction was completed after reacting at 25° C. for 5 h. The reaction was quenched by adding saturated ammonium chloride solution (5 mL). Ethyl acetate was added for extraction (3×5 mL). The aqueous phase and organic phase were separated. The organic phase was dried over anhydrous magnesium sulfate, and dried via rotary evaporation. The residue was separated by column chromatography to obtain 63.7 mg of product as a light brown oil in 43.5% yield.

Preparation of Intermediate I

Compound II: boron trifluoride diethyl etherate:ethyl acetate=1:0.07:122.5.

(5) In a 2 L three-necked flask, compound II (145.5 mg, 0.5 mmol) was dissolved in ethyl acetate (5 mL), a solution of boron trifluoride diethyl etherate (10 mg, 0.07 mmol) in ethyl acetate (1 mL) was added dropwise at a room temperature of 30° C., and then stirred for 0.5 h. The reaction solution was added with ethyl acetate (5 mL), quenched with saturated sodium bicarbonate (10 mL) and partitioned. The solution was washed with saturated brine (10 mL), and the organic phase was separated, dried over anhydrous sodium sulfate, filtered, and dried via rotary evaporation to obtain 130.9 mg of crude product, which was purified by column chromatography to obtain 98.55 mg of compound I as a bright yellow oil in 67.7% yield.

Example 4

Preparation of Compound IV:
Compound VIII: DIBAL-H:dichloromethane=1:1.2:72.0.

(1) In a 20 mL three-necked flask, compound VIII (300 mg, 1.3 mmol) was dissolved in dry dichloromethane (6 mL), the temperature was controlled at −78° C., and DIBAL-H (1 M, 1.54 mL, 1.54 mmol) was slowly added dropwise. The reaction was incubated for 1 h, and the reaction was monitored by TLC until completed. Saturated ammonium chloride solution (10 g) was added and stirred well to form a white solid layer. The white solid layer was diluted by adding ethyl acetate and filtered with diatomaceous earth, and the filtrate was extracted and partitioned with ethyl acetate. The organic phase was dried over anhydrous sodium sulfate, dried via rotary evaporation, and directly used in the next reaction step.

Preparation of Intermediate V

Compound VI: bromoacetone:triethylamine:N,N-dimethylformamide=1:1.2:1.2:23.0.

(2) In a 2 L three-necked flask, compound VI (1.39 g, 8 mmol) and triethylamine (1.01 g, 10 mmol) were added to N,N-dimethylformamide (6.5 mL), and stirred well at a room temperature of 30° C. A solution of bromoacetone (1.39 g, 10 mmol) in N,N-dimethylformamide (8.5 mL) was added slowly under the protection of nitrogen and the reaction was vigorously exothermic. The reaction was stirred for 1 h. The reaction system changed from yellow to brown, and the reaction was monitored by TLC until completed. The solvent was removed by concentration under reduced pressure. The crude product was purified by column chromatography to obtain 0.64 g of compound V in 65.4% yield.

Preparation of Intermediate III

Compound V: hydrogen peroxide:toluene=1:1.0:40.0.

(3) In a 20 mL three-neck flask, compound V (330 mg, 1.48 mmol) was dissolved in toluene (5 mL), the temperature was controlled at −10-0° C., and 30% hydrogen peroxide solution (1.48 mmol) was slowly added dropwise. The reaction was completed after incubating for 1 h. The reaction was quenched by adding saturated sodium thiosulfate solution (20 mL). The aqueous phase and organic phase were separated. The aqueous phase was extracted with dichloromethane (15 mL), and the organic phases were combined. The organic phase was washed twice with saturated sodium bicarbonate solution (10 mL, 15 mL), then washed with saturated sodium chloride solution (10 mL), and dried via rotary evaporation. The residue was separated by column chromatography to obtain 214.11 mg of product as a white solid in 60.7% yield.

Preparation of Intermediate II

Compound III: compound IV: triethylamine:trimethyl phosphite:acetonitrile=1:1.5:2.0:1.0:95.0.

(4) In a 20 mL three-necked flask, compound III (119 mg, 0.5 mmol) was dissolved in acetonitrile (5 mL) and compound IV (176 mg, 0.75 mmol), triethylamine (101 mg, 1.0 mmol) and trimethyl phosphite (62 mg, 0.5 mmol) were added at 25° C. The reaction was completed after reacting at 25° C. for 5 h. The reaction was quenched by adding saturated ammonium chloride solution (5 mL). Ethyl acetate was added for extraction (3×5 mL). The aqueous phase and organic phase were separated. The organic phase was dried over anhydrous magnesium sulfate, and dried via rotary evaporation to obtain 138 mg of crude product, which was separated by column chromatography to obtain 93.24 mg of product as a light brown oil in 63.6% yield.

Preparation of Intermediate I

Compound II: boron trifluoride diethyl etherate:toluene=1:0.07:113.5.

(5) In a 2 L three-necked flask, compound II (145.5 mg, 0.5 mmol) was dissolved in toluene (5 mL), a solution of boron trifluoride diethyl etherate (10 mg, 0.07 mmol) in toluene (1 mL) was added dropwise at a room temperature of 30° C., and then stirred for 0.5 h. The reaction solution was added with toluene (5 mL), quenched with saturated sodium bicarbonate (10 mL) and partitioned. The solution was washed with saturated brine (10 mL), and the organic phase was separated, dried over anhydrous sodium sulfate, filtered, and dried via rotary evaporation to obtain 130.9 mg of crude product, which was purified by column chromatography to obtain 84.14 mg of compound I as a bright yellow oil in 57.8% yield.

The method for the preparation of trans-N-benzyloxycarbonyl-(3-hydroxy-2-piperidinyl)-2-propanone as an intermediate of halofuginone according to the present disclosure has high yields and stable qualities, provides a new reference route for the synthesis of trans-N-benzyloxycarbonyl-(3-hydroxy-2-piperidinyl)-2-propanone, avoids the reduction of pyridine, and overcomes the disadvantage of requiring the use of an expensive metal catalyst Rh/Al$_2$O$_3$.

The above description is only the preferred implementation of the present disclosure, and is not intended to limit the parent scope of the present disclosure, and all equivalent transformations made by the present disclosure are within the scope of patent protection of the present disclosure.

What is claimed is:

1. A method for the preparation of trans-N-benzyloxycarbonyl-(3-hydroxy-2-piperidinyl)-2-propanone as an intermediate of halofuginone, characterized in that the synthetic route thereof is as follows:

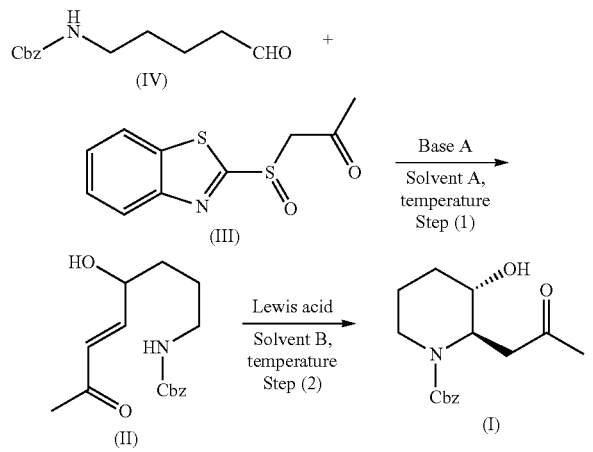

and the synthesis method comprises the following steps:
(1) subjecting amino-substituted pentanal as shown in Formula IV with a thiazolyl sulfoxide compound as shown in Formula III in the presence of a base to a Mislow-Evans rearrangement reaction to obtain α,β-unsaturated ketone as shown in Formula II; and
(2) obtaining trans-N-benzyloxycarbonyl-(3-hydroxy-2-piperidinyl)-2-propanone as shown in Formula I under the catalysis of Lewis acid with the following synthetic route:

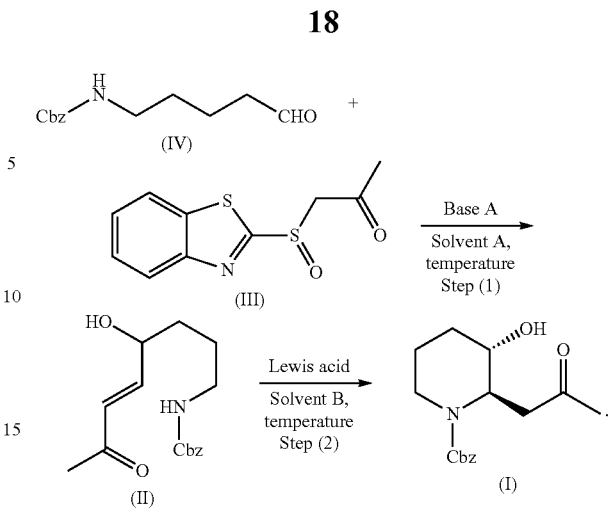

2. The method for the preparation of trans-N-benzyloxycarbonyl-(3-hydroxy-2-piperidinyl)-2-propanone as an intermediate of halofuginone according to claim 1, characterized in that the synthetic route of the thiazolyl sulfoxide compound as shown in Formula III is as follows:

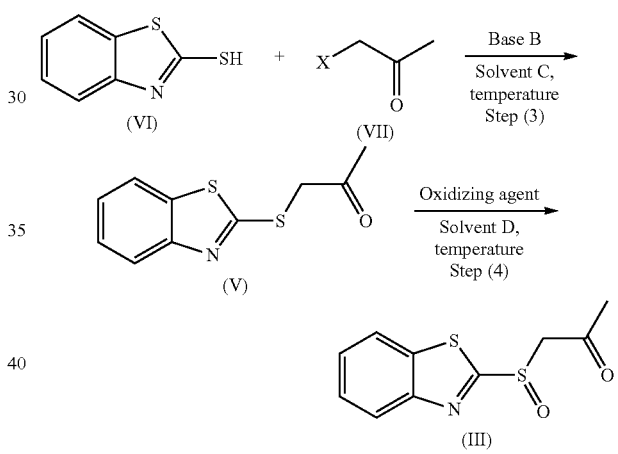

and the synthesis method comprises the following steps:
(1) subjecting a thiazolyl thiol as shown in Formula VI with α-haloacetone as shown in Formula VII to a substitution reaction to obtain thiazolyl thioether as shown in Formula V; and
(2) oxidizing the thiazolyl thioether with an oxidizing agent to obtain the thiazolyl sulfoxide compound as shown in Formula III.

3. The method for the preparation of trans-N-benzyloxycarbonyl-(3-hydroxy-2-piperidinyl)-2-propanone as an intermediate of halofuginone according to claim 1, characterized in that the synthetic route of the amino-substituted pentanal as shown in Formula IV is as follows:

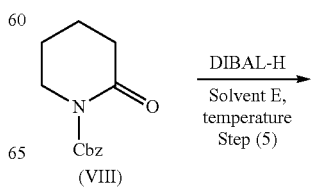

-continued

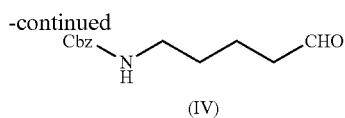

(IV)

and the synthesis method comprises: reducing the piperidone as shown in Formula VIII with DIBAL-H to obtain the amino-substituted pentanal as shown in Formula IV.

4. The method for the preparation of trans-N-benzyloxycarbonyl-(3-hydroxy-2-piperidinyl)-2-propanone as an intermediate of halofuginone according to claim 1, characterized in that in step (1), the organic solvent A is any one or more of dichloromethane, ethanol, isopropanol, acetonitrile, trimethyl phosphite, tetrahydrofuran, N,N-dimethylacetamide, N,N-dimethylformamide or ethyl acetate, and the amount of organic solvent A by mass is 3 to 30 times that of compound VI.

5. The method for the preparation of trans-N-benzyloxycarbonyl-(3-hydroxy-2-piperidinyl)-2-propanone as an intermediate of halofuginone according to claim 1, characterized in that in step (1), the base A as a base is selected from organic bases or inorganic bases, and the organic base is selected from any one of sodium hydride, sodium methoxide, pyridine, piperidine, potassium tert-butoxide, sodium tert-butoxide, butyllithium, 4-dimethylaminopyridine, N,N-diisopropylethylamine or triethylamine; and the inorganic base is selected from any one of sodium hydroxide, potassium hydroxide, potassium carbonate, potassium phosphate or sodium carbonate; and
in step (1), the molar ratio of compound VI, compound VII and base A is 1:(1.0-3.0):(1.0-3.0).

6. The method for the preparation of trans-N-benzyloxycarbonyl-(3-hydroxy-2-piperidinyl)-2-propanone as an intermediate of halofuginone according to claim 1, characterized in that in step (2), the organic solvent B is any one of dichloromethane, ethanol, isopropanol, acetonitrile, trimethyl phosphite, tetrahydrofuran, N,N-dimethylacetamide, N,N-dimethylformamide or ethyl acetate, and the amount of organic solvent B by mass is 2 to 30 times that of compound II; and in step (2), the reaction is carried out at a suitable temperature for a suitable time;
in step (2), the Lewis acid is any one of aluminum trichloride, boron trifluoride diethyl etherate, iron trichloride, and zinc chloride; and
in step (2), the molar ratio of compound II and Lewis acid is 1:(0.05-0.10).

7. The method for the preparation of trans-N-benzyloxycarbonyl-(3-hydroxy-2-piperidinyl)-2-propanone as an intermediate of halofuginone according to claim 2, characterized in that in step (3), the organic solvent C is any one of dichloromethane, ethanol, isopropanol, acetonitrile, tetrahydrofuran, N,N-dimethylacetamide, N,N-dimethylformamide or ethyl acetate, and the amount of organic solvent C by mass is 5 to 50 times that of compound VI;
in step (3), the base B is selected from organic bases or inorganic bases, and the organic base is selected from any one of sodium hydride, sodium methoxide, potassium tert-butoxide, sodium tert-butoxide, butyllithium, 4-dimethylaminopyridine, N,N-diisopropylethylamine or triethylamine; the inorganic base is selected from any one of sodium hydroxide, potassium hydroxide, potassium carbonate, potassium phosphate or sodium carbonate; and X represents any one of chlorine, bromine, and iodine; and
in step (3), the molar ratio of compound VI, haloacetone and base is 1:(1.0-2.0):(1.0-2.0).

8. The method for the preparation of trans-N-benzyloxycarbonyl-(3-hydroxy-2-piperidinyl)-2-propanone as an intermediate of halofuginone according to claim 2, characterized in that
in step (4), the organic solvent D is one of dichloromethane, ethanol, isopropanol, acetic acid, acetonitrile, tetrahydrofuran, N,N-dimethylacetamide, N,N-dimethylformamide or ethyl acetate, and the amount of organic solvent D by mass is 3 to 50 times that of compound V;
in step (4), the oxidizing agent is any one of hydrogen peroxide, m-chloroperoxybenzoic acid, and peroxyacetic acid; and
in step (4), the molar ratio of compound V and oxidizing agent is 1:(0.80-3.0).

9. The method for the preparation of trans-N-benzyloxycarbonyl-(3-hydroxy-2-piperidinyl)-2-propanone as an intermediate of halofuginone according to claim 3, characterized in that in step (5), the organic solvent E is the organic solvent B, which is any one of dichloromethane, 1,2-dichloroethane, ethanol, isopropanol, trifluoroethanol, acetonitrile, tetrahydrofuran or ethyl acetate, and the amount of organic solvent B by mass is 3 to 50 times that of compound VIII.

10. The method for the preparation of trans-N-benzyloxycarbonyl-(3-hydroxy-2-piperidinyl)-2-propanone as an intermediate of halofuginone according to claim 3, characterized in that in step (5), the reducing agent is diisopropylaluminium hydride, and the molar ratio of compound VIII and reducing agent is 1:(1.0-4.0).

* * * * *